United States Patent [19]

Evans et al.

[11] Patent Number: 5,514,538
[45] Date of Patent: May 7, 1996

[54] BICARBONATE ASSAY AND PHOSPHOENOLPYRUVATE CARBOXYLASE ENZYME FROM HYPHOMICROBIUM

[75] Inventors: Christopher T. Evans, Hertfordshire; Richard A. Wisdom, Cambridge, both of England

[73] Assignee: Genzyme Limited, Suffolk, England

[21] Appl. No.: 40,273

[22] Filed: Mar. 30, 1993

Related U.S. Application Data

[63] Continuation of Ser. No. 697,810, May 9, 1991, abandoned.

[30] Foreign Application Priority Data

May 9, 1990 [GB] United Kingdom .................... 9010359

[51] Int. Cl.[6] .............................. C12Q 1/00; C12Q 1/48; C12Q 1/32
[52] U.S. Cl. .................................... 435/4; 435/15; 435/26; 435/975
[58] Field of Search ..................... 435/4, 14, 15, 435/26, 194, 975; 436/8, 18

[56] References Cited

U.S. PATENT DOCUMENTS 5,112,740  5/1992  Nealon ........................................ 435/15

5,116,728  5/1992  Crowther ................................... 435/14

FOREIGN PATENT DOCUMENTS 0076478  4/1983  European Pat. Off. .
358940   3/1990  European Pat. Off. .

OTHER PUBLICATIONS

Doronina, N. V., The Properties of a New Hyphomicrobium Microbiologiya, 54 (4) 1985 pp. 538–544. (English).
Plant Physiology, vol. 57, 1976, pp. 906–910 "Purification & Characterization of PEPC from Maize Leaves".
Applied And Environmental Microbiology, vol. 40, No. 2, Aug. 1980, pp. 370–375. "Regulation of Enzymes Assoc. w C–1 Metabolism in 3 Facultative Methylotrophs".

Primary Examiner—Ralph J. Gitomer
Attorney, Agent, or Firm—Foley & Lardner

[57] ABSTRACT

Phosphoenolpyruvate carboxylase (PEPC) characterised by a specific activity of at least 40 units/mg; and/or by no more than 50% loss of activity after 60 days in 167 mM Tricine/HCl buffer, pH 8.0, and 15 mM $MgCl_2$; and/or, at pH 6.5, an activity of at least 40% relative to the activity at optimum pH is disclosed. Such enzymatic activity can be obtained from serine pathway methylotrophs such as Hyphomicorbium, and is very suitable for use in measuring bicarbonate in biological samples.

28 Claims, No Drawings

BICARBONATE ASSAY AND PHOSPHOENOLPYRUVATE CARBOXYLASE ENZYME FROM HYPHOMICROBIUM

This application is a continuation of application Ser. No. 07/697,810, filed May 9, 1991, now abandoned.

FIELD OF THE INVENTION

This invention relates to the enzyme phosphoenolpyruvate carboxylase (PEPC) and to its preparation.

BACKGROUND OF THE INVENTION

PEPC is useful in the measurement of bicarbonate in biological samples. When this enzyme is linked to malate dehydrogenase, the concentration of bicarbonate is directly proportional to the consumption of oxaloacetate and NADH, as follows (MDH=malate dehydrogenase; PEP phosphoenolpyruvate):

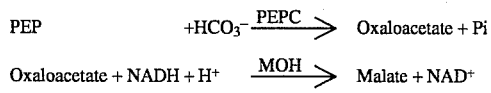

The most popular commercial sources of PEPC are Zea maize and wheat germ. From both sources, the PEPC has poor intrinsic stability (i.e. in the absence of stabiliser), there are inconsistencies in the raw material, and batch-to-batch variation occurs in the quality of the final product. Further the PEPC may be obtained together with PEP-degrading enzymes which may affect the stability of the assay kit.

It would be desirable if PEPC could be obtained from more consistent raw material, and that there should be no seasonal limitations on raw materials. Further, there would desirably be simpler purification, less significant contaminating enzymes, more liquid stability, and increased activity. Commercially-available PEPC usually has a specific activity of about 5 units/mg, although activities of 20–22 units/mg protein have been claimed.

SUMMARY OF THE INVENTION

Strains of serine pathway methylotrophs which are hyper-producers of PEPC, have been identified. The isolated enzyme shows intrinsic enhanced liquid stability, a broad pH profile and high purity. It is thus suitable for producing a superior diagnostic reagent for the measurement of bicarbonate in biological fluids.

Novel PEPC according to this invention has a relatively high specific activity, for purified protein, of at least 40, e.g. 50–100 units/mg protein.

The novel PEPC is from a microbial source, and does not suffer from the disadvantages associated with plant sources. It has a relatively high $K_m$, and can therefore be used in kinetic assays, by rate methodology; to date, end-point assays have been more usual.

The novel PEPC also has a relatively high stability, e.g. losing no more than 50%, preferably no more than 25%, activity after 10 days in 100 mM Tris-HCl buffer, pH 8.0, and 15 mM $MgCl_2$, at 25° C. It does not require the SH-containing stabilisers such as glutathione required by PEPC from, say, Zea maize.

The novel PEPC has, as an especially valuable characteristic, a pH profile such that, at pH 6.5 (a preferred condition of use), its activity is at least 40%, preferably at least 50%, e.g. up to 75%, 90% or more, relative to the activity at optimum pH.

DESCRIPTION OF THE INVENTION

The advantages of the invention are apparently associated with enzymes obtained from serine pathway methylotrophic bacteria. Suitable genera of PEPC-containing methylotrophs are Hyphomicrobium, Pseudomonas sp. and Methylomonas.

For example, strains of the microorganism genus Hyphomicrobium have been isolated and grown in fermentation using methanol and methylamine or trimethylamine as carbon and nitrogen sources. The enzyme from such a strain has been purified.

A strain of Hyphomicrobium, identified as ENZA-30, has been deposited in accordance with the provisions of the Budapest Treaty, at the National Collection of Industrial Bacteria, on 04.05.90. The accession number is NCIMB 40280.

Yields and specific activities, and also other characteristics, may be improved by selection procedures, e.g. after mutagenesis. This invention includes mutants of the deposited and wild-type serine pathway methylotrophs. Conventional mutagens such as NTG, EMS or UV light may be used.

Although its preparation from microorganisms has been described, it is anticipated that PEPC of the invention may be prepared by cloning. This may be done by conventional techniques.

PEPC of the invention can conveniently be freeze-dried, in which form it retains good activity. It may be formulated as a powder, e.g. together with trehalose and/or buffer salts. Alternatively, as indicated above, it retains good activity in liquid form, e.g. in tricine buffer, at pH 6.5–8, e.g. pH 7.

For use in assaying bicarbonate in biological samples, the PEPC may be provided in a formulation together with the substrate PEP, MDH, NADH, $Mg^{2+}$ ions and a buffer, pH 5–10, e.g. 6.5–8. Such a formulation may be freeze-dried, before reconstitution with freshly-distilled, boiled water free of $CO_2$ or buffer. The enzyme and substrates can also be provided in separate containers of an assay kit.

In the assay, serum is added to the given components, and the decrease in absorbance at 340 nm, as NADH is converted, is measured. This decrease is directly proportional to the concentration of bicarbonate in the serum.

The following Example illustrates fermentation of a PEPC-producing strain according to the invention.

Example 1

Cells of Hyphomicrobium sp. NCIMB 40280 are transferred from an agar plate into a 2 l flask containing 500 ml of medium. After shaking for 36 hours the contents are transferred into 12.5 l medium in a seed fermenter. This is then grown aerobically for 14 hours after which the contents are transferred into the production fermenter containing 375 l of medium. The fermentation is continued until the carbon source has been exhausted, about 16 hours, after which feeding is started. The time for starting the feed is signified by a drop in the oxygen demand in the fermenter. At this time a pulse of feed is automatically added to bring the methylamine concentration to about 90 mMolar. When this carbon has been utilised a further pulse is added. This pulsed addition is maintained until all the feed (100 l) has been added. By feeding in this fashion, the methylamine concentration in the fermenter does not build up and become toxic.

The media for seed growth and initial batch growth in the production fermenter are the same excepting that an additional 15 g/l agar is added to make the seed plates. All fermentations are carried out at 30° C.

| Media: | |
|---|---|
| Monomethylamine Phosphate | 87 mMolar |
| Ammonium sulphate | 2 g/l |
| Dipotassium hydrogen phosphate | 1.5 |
| Sodium dihydrogen phosphate $2H_2O$ | 0.5 |
| Magnesium sulphate $7H_2O$ | 1.0 |
| Yeast extract | 1.0 |
| Bacteriological peptone | 1.0 |
| Trace element solution | 0.5 ml/l |
| Deionised water | balance |
| The feed medium: | |
| Monomethylamine phosphate | 2.5 Molar |
| Yeast extract | 2.0 g/l |
| Dipotassium hydrogen phosphate | 1.5 g/l |
| Sodium dihydrogen phosphate $2H_2O$ | 0.5 g/l |
| Trace element solution | 4 ml/l |
| Deionised water | balance |
| The trace element solution: | |
| $FeSO_4.7H_2O$ | 2 g/l |
| $CaCl_2.2H_2O$ | 5.3 |
| $MnSO_4.H_2O$ | 0.2 |
| $ZnSO_4.7H_2O$ | 0.2 |
| $CuSO_4.5H_2O$ | 0.04 |
| $CoCl_2.6H_2O$ | 0.04 |
| $Na_2Mo_3O_4$ | 0.04 |
| $H_3BO_3$ | 0.03 |

The pH of the medium is adjusted to 7.0 prior to sterilisation and maintained during fermentation by the addition of 4N sodium hydroxide or 20% phosphoric acid as required. The monomethylamine phosphate is filter-sterilised as a concentrated aqueous solution separately from the other components. The feed is filter-sterilised directly into the fermenter.

After growth, the cells are harvested in a continuous disc stack centrifuge.

By way of example, the purification of PEPC begins with a detergent lysis and is followed by column chromatography, concentration and dialysis, followed by simple sugar formulation and freeze-drying. The scheme is illustrated in the following Example.

Example 2

(a) Lysis is performed with a solution of Triton X-100, a non-ionic detergent. It is added to resuspended cells (10% w/v) at 1% v/v. Lysis usually takes about 1 to 1.5 hours at 15° to 20° C. Once lysis is complete, the cell debris is removed by centrifugation with the aid of streptomycin sulphate.

(b) Column chromatography involves the use of a strong anion exchanger such as Fractogel-TMAE, DEAE sepharose, Q sepharose, DE 52 or QA 52.

For a large volume of enzyme solution, the absorption can be is carried out as a batch up-take. The gel also has a batch wash prior to packing into the column for a gradient elution.

The gradient is of increasing salt concentration. The active fractions are pooled to give a specific activity of >30 U/mg but some fractions contain enzyme of 60 U/mg protein.

The enzyme may be held on the gel overnight; no loss of activity is seen. If stored for longer, then the recoveries begin to decrease. Typical results are shown in Table 1:

TABLE 1

| Days stored | Total recovery (%) | Pool S/A (U/mg) |
|---|---|---|
| 0 | 91 | 37.4 |
| 2 | 85 | 33.0 |
| 4 | 76 | 28.1 |
| 8 | 60 | 26.9 |

(c) Concentration involves the use of a tangential flow system. If concentrated to approximately 300 U/ml, there is usually about 1.0 l from the 10 l column pool. The protein concentration can be taken as high as 12 mg/ml without adverse effect.

(d) Dialysis reduces the salt concentration. Typically, a 1.0 l solution is dialysed against 100 l of buffer, and the enzyme solution clarified by centrifugation. The clarified solution is then filtered. Some precipitation may be seen at this stage. This precipitation does not effect the enzyme activity and recovery from dialysis is usually between 95 and 98%.

(e) Formulation involves only the addition of trehalose (1 mg/ml). This gives good results upon resuspension in terms of clarity and stability of the enzyme. The presence of salt at 0.15M is also found to help solubilisation and subsequent stability.

Lyophilised PEPC powder is obtained, having the following characteristics:

| Powder activity | >10 U/mg | |
|---|---|---|
| Specific activity | >25 U/mg | Protein |
| Ass. activities | NADH - ox | <0.02% |
| | LDH | <0.05% |
| | PK | <0.5% |

Stability trials have been conducted on lyophilised enzyme, at 4° C., 25° C. and 37° C. Results are shown in Table 2: (NT=not tested)

TABLE 2

| Time | % activity recoverd at | | |
|---|---|---|---|
| (days) | 4° C. | 25° C. | 37° C. |
| 0 | 100 | 100 | 100 |
| 3 | NT | 95 | 97 |
| 7 | 83 | 83 | 87 |
| 10 | NT | 94 | 91 |
| 18 | 92 | 88 | 90 |
| 24 | NT | 90 | 87 |
| 50 | 114 | NT | NT |
| 77 | 110 | NT | NT |

All recoveries are based on specific activity to rule out weighing errors. The powder is very stable at 4° C. and there is only a slight decrease in activity at 25° C. and 37° C. with time.

The results of reconstituted enzyme at 37° C., 25° C. and 4° C. with azide are shown in Table 3:

TABLE 3

| Time | % activity recovered at | | |
|---|---|---|---|
| (days) | 4° C. | 25° C. | 37° C. |
| 4 | 94 | 104 | 2 |
| 7 | 96 | 92 | 0 |

TABLE 3-continued

| Time | % activity recovered at | | |
|---|---|---|---|
| (days) | 4° C. | 25° C. | 37° C. |
| 14 | 94 | 93 | — |
| 30 | 100 | 86 | — |
| 42 | 105 | 85 | — |
| 63 | 105 | 66 | — |

The enzyme was stored in assay buffer (167 mM Tricine/HCl with 15 mM $MgCl_2$, pH 8.0).

There are a number of pH effects on PEPC, most of which depend on the buffer that has been used. Through various trials it was discovered that at pH 7.0 Bis-tris buffer gave better stability and activity than the normally used Tricine buffer. The stability of the enzyme when at pH 7.0 is recorded in Table 4:

TABLE 4

| Time (days) | 4° C. | 25° C. |
|---|---|---|
| 7 | 111 | 110 |
| 12 | 97 | 85.5 |
| 14 | 111 | 96 |
| 15 | 89 | 83 |

For pH 6.0, 8.0 and 9.0, 150 mM Tricine+1 mM $MgCl_2$ was used. For pH 7.0 150 mM bis-tris+1 mM $MgCl_2$ was chosen. Solutions were stored at 25° C. Results for pH stability are given in Table 5:

TABLE 5

| Time | % activity recovered at | | | |
|---|---|---|---|---|
| (days) | pH 6 | pH 7 | pH 8 | pH 9 |
| 7 | 69 | 99 | 81.8 | 78.2 |
| 12 | 45.5 | 78.2 | 67.3 | 56.4 |

The effect of pH on the enzyme activity was checked by changing the buffers as well as pH values. Once again, at pH 7 Bis-tris was used. The results are shown in Table 6:

TABLE 6

| pH | % activity recovered |
|---|---|
| 6 | 65.5 |
| 6.5 | 74.5 |
| 7.0 | 100 |
| 8.0 | 88.2 |
| 9.0 | 74.5 |

The buffer normally used in the bicarbonate assay is 150 mM Tricine and 1 mM $MgCl_2$, pH 8.0. The activity results suggest that 150 mM Bis-tris buffer at pH 7.0 would be better.

Low concentrations of calcium have an inhibitory effect on the PEPC activity. $Mg^{2+}$ seems to be the only effective activator of the enzyme, and works better as the chloride compound than as the sulphate.

The Km's of Hyphomicrobium PEPC were checked with both sodium bicarbonate and phosphoenol pyruvate as substrates. The effect of various pH values and temperature were investigated.

The effect of bicarbonate on the activity of PEPC was evaluated at pH 8.0 in 167 mM Tricine buffer+1 mM $MgCl_2$. The Km was 1.3 mM. This is high due to inference of dissolved carbon dioxide from the atmosphere. It is probably below 1 mM in this buffer.

The Km values of the monocyclohexylammonium salt and tricyclohexylammonium PEP salts at pH 7.0 and 25° C. were found to be very similar. The result is 0.91 mM for the tricyclohexylammonium salt.

The effect of temperature on the activity of PEPC was evaluated. Lyophilised enzyme was resuspended in 167 mM tricine buffer pH 7.0 containing 1 mM $MgCl_2$ at a concentration of 300 u/l. The enzyme was then assayed at the desired temperature using the recommended reagents.

The relative activity rose from approximately 10% at 20° C. to 100% at 50° C., and then fell rapidly to about 10% at 55° C.

The effect of pH on the activity of PEPC was evaluated. Lyophilised enzyme was resuspended (10 mg/ml) in 167 mM Tricine pH 8.0 (+1 mM $MgCl_2$) and diluted to a concentration of 1 u/ml. The enzyme was then assayed in the following buffer systems. At pH 6.0, 8.0 and 9.0 Tricine (150 mM) was used. At pH 6.5 and 7.0 bis-tris (150 mM) was used.

The relative activity was approximately 70%, 85%, 115%, 100% and 90%, at pH 6.0, 6.5, 7.0, 8.0 and 9.0, respectively.

The following Example illustrates the phosphoenolpyruvate carboxylase assay.

Example 3

Reagents:

A 167 mM Tricine. HCl buffer, pH 8.0, containing 16.7 mM $MgCl_2$

B 20.7 mM sodium bicarbonate in Reagent A

C 217 mM phosphoenolpyruvate in Reagent A

D 10 mM NADH solution, the concentration of which is checked in the following way:
  1 Dispense 0.98 ml of Reagent A into a cuvette and zero a spectrophotometer set at 340 nm with this cuvette
  2 Add 0.02 ml of Reagent D to this cuvette and mix thoroughly
  3 The $A_{340}$ of this solution must be 1.14 to 1.185

E 700 U/ml malate dehydrogenase

Method:

1 Adjust spectrophotometer to 340 nm and 25° C.

2 Prepare a reagent cocktail as follows:
  Into a 50 ml beaker dispense; 46.0 ml Reagent B 1.0 ml Reagent C
  This cocktail is stable for 8 hr when stored at 4° C.

3 Dispense 0.94 ml of the reagent cocktail into a cuvette together with 0.02 ml of Reagent D, and 0.02 ml of Reagent E Incubate the cuvette in the spectrophotometer at 25° C. to attain temperature equilibration and then establish background rate, if any 4 Dilute the enzyme to approximately 1.5 U/ml in reagent A, and initiate the reaction by adding 0.02 ml of this solution to the cuvette 5 Calculate the change in absorbance ($\Delta A$/rain) over the linear portion of the reaction $$\text{Activity (U/ml)} = \frac{(\Delta A/\text{min}) \text{ (total cell vol.) (enz. diln.)}}{6.22 \times \text{(Sample vol.)}}$$

($E_{mM}$ NADH = 6.22)

We claim:

1. Purified phosphoenolpyruvate carboxylase (PEPC), wherein said PEPC has, at pH 6.5, an activity of at least 40% relative to its activity at pH 8.0 in 150 mM Tricine buffer.

2. Purified PEPC according to claim 1, wherein the PEPC has, at pH 6.5, an activity of at least 50% of its activity at pH 8.0 in 150 Mm Tricine buffer.

3. Purified PEPC according to claim 1, wherein said PEPC has a specific activity of at least 40 U/mg protein.

4. Purified PEPC according to claim 1, of microbial origin.

5. Purified PEPC according to claim 1, isolated from a strain of a serine pathway methylotrophic bacterium.

6. Purified PEPC according to claim 1, wherein said strain is Hyphomicrobium.

7. Purified PEPC according to claim 6, wherein said Hyphomicrobium strain has the characteristics of that available as NCIMB 40280.

8. Purified Phosphoenolpyruvate carboxylase (PEPC), wherein said PEPC has no more than 50% loss of activity after 60 days in 167 mM Tricine/HCL aqueous buffer, pH 8.0, and 15 mM $MgCl_2$, at 25° C., in the absence of stabilizer.

9. Purified phosphoenolpyruvate carboxylase (PEPC) having at least 2 of the characteristics selected from the group consisting of (i) at pH 6.5, an activity of at least 40% relative to its activity at pH 8.0 in 150 mM Tricine buffer, (ii) at pH 6.5, an activity of at least 50% relative to its activity at pH 8.0 in 150 mM Tricine buffer, (iii) a specific activity of at least 40 U/mg protein, and (iv) having no more than 50% loss of activity after 60 days in 167 mM Tricine/HCL aqueous buffer, pH 8.0, and 15 mM $MgCl_2$, at 25° C., in the absence of stabilizer.

10. A composition, for measuring bicarbonate in biological samples, comprising purified PEPC according to claim 1, malate dehydrogenase, phosphoenolpyruvate (PEP), buffer (pH 5–10) and NADH.

11. An assay for measuring bicarbonate in a biological sample, comprising the steps of:

(a) mixing said biological sample with a composition comprising PEPC which has an activity at pH 6.5 of at least 40% of its activity at pH 8.0 in 150 mM Tricine buffer, PEP, malate dehydrogenase, the reduced form of nicotinamide adenine dinucleotide (NADH) and a buffer, at a pH at or below 7; and (b) measuring the change in absorbance of light corresponding to the disappearance of NADH.

12. An assay as claimed in claim 11, wherein said sample and composition comprising PEPC are mixed at a pH within the range of 6 to 7.

13. An assay as claimed in claim 12, wherein said sample and composition comprising PEPC are mixed at a pH of about 6.5.

14. An assay as claimed in claim 11, wherein the PEPC has an activity, at pH 6.5 of at least 50% of its activity at pH 8.0 in 150 mM Tricine buffer.

15. An assay as claimed in claim 14, wherein said PEPC is isolate from a strain of a serine pathway methylotrophic bacterium.

16. An assay as claimed in claim 15, wherein said strain is Hyphomicrobium.

17. An assay as claimed in claim 16, wherein said Hyphomicrobium strain has the characteristics of that available as NCIMB 40280.

18. In an assay for measuring bicarbonate in biological samples under carboxylation conditions at or below pH 7, wherein the rate of the carboxylation reaction of phosphoenolpyruvate in the presence of PEPC is directly or indirectly measured and related to the bicarbonate concentration in the sample, the improvement wherein a PEPC is used which has an activity at pH 6.5 of at least 40% of its activity at pH 8,0 in 150 mM Tricine buffer.

19. An assay as claimed in claim 18, wherein the bicarbonate is measured in said biological samples under carboxylation conditions at a pH within the range of 6 to 7.

20. An assay as claimed in claim 19, wherein the bicarbonate is measured in said biological samples under carboxylation conditions at a pH of about 6.5.

21. An assay as claimed in claim 18, wherein the PEPC has an activity, at pH 6.5 of at least 50% of its activity at pH 8,0 in 150 mM Tricine buffer.

22. An assay as claimed in claim 18, wherein said PEPC is a strain of a serine pathway methylotrophic bacterium.

23. An assay as claimed in claim 22, wherein said strain is Hyphomicrobium.

24. An assay as claimed in claim 23, wherein said Hyphomicrobium strain has the characteristics of that available as NCIMB 40280.

25. An assay for measuring bicarbonate in a biological sample, comprising the steps of:

(a) mixing said biological sample with a composition comprising PEPC which has a specific activity of at least 40 U/rag protein, PEP, malate dehydrogenase, NADH and a buffer; and (b) measuring the change in absorbance of light corresponding to the disappearance of NADH.

26. An assay for measuring bicarbonate in a biological sample, comprising the steps of:

(a) mixing said biological sample with a composition comprising (i) PEPC characterized by no more than 50% loss of activity after 60 days in 167 mM Tricine/HCl aqueous buffer, pH 8.0, and 15 mM $MgCl_2$, at 25° C., in the absence of stabilizer, (ii) PEP, (iii) malate dehydrogenase, (iv) NADH and (v) a buffer; and (b) measuring the change in absorbance of light corresponding to the disappearance of NADH.

27. In an assay for measuring bicarbonate in biological samples under carboxylation conditions, wherein the rate of the carboxylation reaction of phosphoenolpyruvate in the presence of PEPC is directly or indirectly measured and related to the bicarbonate concentration in the sample, the improvement wherein a PEPC is used which has an activity of at least 40 U/mg protein.

28. In an assay for measuring bicarbonate in biological samples under carboxylation conditions, wherein the rate of the carboxylation reaction of phosphoenolpyruvate in the presence of PEPC is directly or indirectly measured and related to the bicarbonate concentration in the sample, the improvement wherein a PEPC is used which is characterized by no more than 50% loss of activity after 60 days in 167 mM Tricine/HCL aqueous buffer, pH 8.0, and 15 mM$MgCl_2$, at 25° C. in the absence of stabilizer.

* * * * *